ized) United States Patent
Babino et al.

(10) Patent No.: US 6,365,124 B1
(45) Date of Patent: Apr. 2, 2002

(54) COMPOSITIONS FOR DETECTING AND SURGICALLY REMOVING LYMPHOID TISSUE INVOLVED IN TUMOR PROGRESSION

(75) Inventors: Alvaro Babino; Eduardo Osinaga, both of Montevideo (UY); Emilio Barbera-Guillem, Powell, OH (US)

(73) Assignee: Biocrystal, Ltd., Westerville, OH (US)

( * ) Notice: Subject to any disclaimer, the term of this patent is extended or adjusted under 35 U.S.C. 154(b) by 0 days.

(21) Appl. No.: 09/244,592

(22) Filed: Feb. 4, 1999

Related U.S. Application Data

(60) Provisional application No. 60/073,882, filed on Feb. 6, 1998, and provisional application No. 60/077,970, filed on Mar. 13, 1998.

(51) Int. Cl.⁷ ................. A61K 51/08; A61B 5/055; C07K 16/30; C07K 16/28
(52) U.S. Cl. ................. 424/1.69; 424/9.34; 530/300; 530/350; 530/387.1; 530/387.7; 530/391.3; 530/402; 530/324; 530/325; 530/326; 530/327; 530/345; 514/2; 514/12; 514/13; 514/14; 514/15
(58) Field of Search ................. 530/300, 350, 530/387.1, 387.3, 387.5, 387.7, 391.3, 402, 324, 325, 326, 327, 345; 424/1.69, 9.34; 514/2, 12, 13, 14, 15

(56) References Cited

U.S. PATENT DOCUMENTS 5,993,813 A * 11/1999 Mezes et al.

FOREIGN PATENT DOCUMENTS

WO    WO 89/01783    * 3/1989

OTHER PUBLICATIONS

Kjeldsen, T. et al. Preparation and characterization on monoclonal antibodies directed to the tumor–associated O–linked sialosyl–2–6 alpha–N–acetylgalactosaminyl (sialosyl–tn) epitope. Cancer Research, 48:(8): 2214–2220. Abstract Only, Apr. 1988.*

Burgess, W.H. et al. Possible dissociationof the heparin–binding and mitogenic activities of heparin–binding (acidic fibroblast) growth factor–1 from its receptor–binding activities by site–directed mutagenesis of a single lysine residue. J. Cell Biolog, Nov. 1990.*

Lazar, E. et al. Transforming growth factor alpha: mutation of aspartic acid 47 and leucine 48 results in different biological activities. Molecular and Cellular Biology, 8(3): 1247–1252, Mar. 1988.*

* cited by examiner

Primary Examiner—Anthony C. Caputa
Assistant Examiner—Anne L. Holleran

(57) ABSTRACT

Compositions are provided for detecting Tn antigen expressing-shed tumor antigen. The compositions include peptides having binding specificity for the Tn antigen; and a detector molecule comprising a peptide, according to the present invention, which is bound to a detectable label. The compositions may be used in a method to detect lymphoid tissues containing shed tumor antigen expressing the Tn antigen.

5 Claims, 5 Drawing Sheets

SEQUENCE LISTING

<160> NUMBER OF SEQ ID NOS: 6

<210> SEQ ID NO 1
<211> LENGTH: 116
<212> TYPE: PRT
<213> ORGANISM: Artificial
<220> FEATURE:
<221> NAME/KEY:
<222> LOCATION:
<223> OTHER INFORMATION: synthesized

<400> SEQUENCE: 1

```
Gln Val Gln Leu Gln Gln Ser Asp Ala Glu Leu Val Lys Pro Gly
 1               5                  10                  15

Ala Ser Val Lys Ile Ser Cys Lys Ala Ser Gly Tyr Thr Phe Thr
                20                  25                  30

Asp His Ala Ile His Trp Val Lys Gln Lys Pro Glu Gln Gly Leu
                35                  40                  45

Glu Trp Ile Gly Tyr Phe Ser Pro Gly Asn Gly Asp Ile Lys Tyr
                50                  55                  60

Asn Glu Lys Phe Lys Gly Lys Ala Thr Leu Thr Ala Asp Lys Ser
                65                  70                  75

Ser Ser Thr Ala Tyr Met Gln Leu Asn Ser Leu Thr Ser Glu Asp
                80                  85                  90

Ser Ala Val Tyr Phe Cys Lys Arg Ser Tyr Gly Asn Tyr Asp Tyr
                95                 100                 105

Trp Gly Gln Gly Thr Thr Leu Thr Val Ser Ser
               110                 115
```

<210> SEQ ID NO 2
<211> LENGTH: 90
<212> TYPE: PRT
<213> ORGANISM: Artificial
<220> FEATURE:
<221> NAME/KEY:
<222> LOCATION:
<223> OTHER INFORMATION: synthesized

<400> SEQUENCE: 2

```
Tyr Thr Phe Thr Asp His Ala Ile His Trp Val Lys Gln Lys Pro
 1               5                  10                  15

Glu Gln Gly Leu Glu Trp Ile Gly Tyr Phe Ser Pro Gly Asn Gly
                20                  25                  30

Asp Ile Lys Tyr Asn Glu Lys Phe Lys Gly Lys Ala Thr Leu Thr
                35                  40                  45

Ala Asp Lys Ser Ser Ser Thr Ala Tyr Met Gln Leu Asn Ser Leu
                50                  55                  60

Thr Ser Glu Asp Ser Ala Val Tyr Phe Cys Lys Arg Ser Tyr Gly
                65                  70                  75

Asn Tyr Asp Tyr Trp Gly Gln Gly Thr Thr Leu Thr Val Ser Ser
                80                  85                  90
```

<210> SEQ ID NO 3
<211> LENGTH: 46
<212> TYPE: PRT
<213> ORGANISM: Artificial
<220> FEATURE:
<221> NAME/KEY:
<222> LOCATION:
<223> OTHER INFORMATION: synthesized

<400> SEQUENCE: 3

Tyr Thr Phe Thr Asp His Ala Ile His Trp Val Lys Gln Lys Pro
1               5                   10                  15

Glu Gln Gly Leu Glu Trp Ile Gly Tyr Phe Ser Pro Gly Asn Gly
                20                  25                  30

Asp Ile Lys Tyr Asn Glu Lys Phe Lys Gly Lys Ala Thr Leu Thr
                35                  40                  45

Ala

<210> SEQ ID NO 4
<211> LENGTH: 75
<212> TYPE: PRT
<213> ORGANISM: Artificial
<220> FEATURE:
<221> NAME/KEY:
<222> LOCATION:
<223> OTHER INFORMATION: synthesized

<400> SEQUENCE: 4

Tyr Thr Phe Thr Asp His Ala Ile His Trp Val Lys Gln Lys Pro
1               5                   10                  15

Glu Gln Gly Leu Glu Trp Ile Gly Tyr Phe Ser Pro Gly Asn Gly
                20                  25                  30

Asp Ile Lys Tyr Asn Glu Lys Phe Lys Gly Lys Ala Thr Leu Thr
                35                  40                  45

Ala Asp Lys Ser Ser Ser Thr Ala Tyr Met Gln Leu Asn Ser Leu
                50                  55                  60

Thr Ser Glu Asp Ser Ala Val Tyr Phe Cys Lys Arg Ser Tyr Gly
                65                  70                  75

<210> SEQ ID NO 5
<211> LENGTH: 75
<212> TYPE: PRT
<213> ORGANISM: Artificial
<220> FEATURE:
<221> NAME/KEY:
<222> LOCATION:
<223> OTHER INFORMATION: synthesized

<400> SEQUENCE: 5

Gln Val Gln Leu Gln Gln Ser Asp Ala Glu Leu Val Lys Pro Gly
1               5                   10                  15

Ala Ser Val Lys Ile Ser Cys Lys Ala Ser Gly Tyr Thr Phe Thr
                20                  25                  30

Asp His Ala Ile His Trp Val Lys Gln Lys Pro Glu Gln Gly Leu
                35                  40                  45

Glu Trp Ile Gly Tyr Phe Ser Pro Gly Asn Gly Asp Ile Lys Tyr
                50                  55                  60

Asn Glu Lys Phe Lys Gly Lys Ala Thr Leu Thr Ala Asp Lys Ser
                65                  70                  75

<210> SEQ ID NO 6
<211> LENGTH: 42
<212> TYPE: PRT
<213> ORGANISM: Artificial
<220> FEATURE:
<221> NAME/KEY:
<222> LOCATION:
<223> OTHER INFORMATION: synthesized

<400> SEQUENCE: 6

-continued

```
Tyr Thr Phe Thr Asp His Ala Ile His Trp Val Lys Gln Lys Pro
1               5                   10                  15

Glu Gln Gly Leu Glu Trp Ile Gly Tyr Phe Ser Pro Gly Asn Gly
                20                  25                  30

Asp Ile Lys Tyr Asn Glu Lys Phe Lys Gly Lys Ala
                35                  40
```

COMPOSITIONS FOR DETECTING AND SURGICALLY REMOVING LYMPHOID TISSUE INVOLVED IN TUMOR PROGRESSION

This is a nonprovisional application based on earlier copending provisional applications Ser. No. 60/073,882 filed Feb. 6, 1998, and reference.

FIELD OF THE INVENTION

The present invention is related to compositions which may be used in methods for detection and/or surgical therapy associated with solid, non-lymphoid tumor types. More particularly, the present invention is related to peptides having binding specificity for shed mucin, and their use for detecting lymphoid tissues, which contain deposits of shed mucin, and which are involved in promotion of tumor cell invasion and metastasis.

BACKGROUND OF THE INVENTION

1. Immunopathology

The response of an individual to tumor cells involves the reactions and counteractions mediated by both cellular and humoral arms of the immune system. Tumor cell growth may represent a disturbance in the equilibrium of the immune system that is pre-existing, and/or induced by the tumor cells themselves. However, most investigations to date have focused on the role of T cells in tumor immunity. The role of B cells in a tumor-bearing individual still remains unclear.

Previous studies have shown that lymph nodes regional to a primary tumor in cancer patients, and in in vivo experimental animal models of tumor development, can undergo a prominent expansion in the germinal centers of immune cells that include B lymphocytes (B cells) (Eremin et al., 1980, Br. J. Cancer 41:62; Bertschmann et al., 1984, Br. J. Cancer 49:477–484). However, the reason(s) for this observed B cell proliferative response remains unclear, and may be due to either activation and stimulation directly by tumor cells or tumor cell components, and/or indirectly by stimulation of T-helper cells which then activate and stimulate B cells. A recent study confirmed the increase in the number of B cells in lymph nodes regional to primary tumors (Ito et al., 1996, Immunobiol. 195:1–15). The number of B cells increase in the regional lymph nodes concomitantly with tumor development, and such B cells appear to be able to elicit anti-tumor immunity. In that regard, there are numerous reports that cancer patients have circulating antitumor antibodies (see, e.g., Carey et al., 1976, Proc. Natl. Acad. Sci. USA 73:3278–3282; Abe et al., 1989, Cancer Res. 80:271–276; Christensen et al., 1989, Int. J. Cancer 37:683–688). Thus, there appears that a humoral immune response towards tumor-associated antigens can be mounted in cancer patients. However, the role of the B cells in the host response to tumor, and the tumor associated antigens recognized by B cells, remain poorly defined.

2. Current Diagnostic and Therapeutic Implications

Several techniques, such as radioimmunodiagnosis and radioimmunoguided surgery, have been developed for the purpose of detecting tumors occult to other imaging techniques. In radioimmunodiagnosis, a patient is injected intravenously with a radiolabeled antitumor monoclonal antibody or radiolabeled antibody fragment with binding specificity for the tumor. Hours to days post-injection, the patient is then examined by immunoscintigraphy for body imaging of primary tumor and metastases. Radioimmunodiagnosis continues to be evaluated for preoperative evaluation of patients (Ryan, 1993, Cancer 71:4217–24). In radioimmunoguided surgery, a patient is injected with a radiolabeled anti-tumor monoclonal antibody, and exploratory surgery is carried out approximately 3–4 weeks post-injection. The 3 to 4 week period allows for the patient to clear radioactivity that is unbound to tumor cells ("background signal"). The surgeon uses a hand-held radiation detector to detect localized high counts of radioactivity representing tumor foci. These radioactive areas subsequently found visually or histologically to contain tumor cells are then resected or excised. U.S. Pat. No. 4,782,840 describes the radioimmunoguided surgery protocol in more detail. Another radioimmunoguided surgery protocol using antibody fragments for close range tumor detection, in detecting and defining tumor and tumor margins, is described in more detail in U.S. Pat. No. 5,716,595.

Using either radioimmunodiagnosis (RAIDS) or radioimmunoguided surgery (RIGS) to search for metastases from colorectal or ovarian cancer, false positivity of draining lymph nodes has been observed (for a review, see Cornelius and West, 1996, J. Surg. Oncol. 63:23–35; Stephens et al., 1993, J. Nucl. Med. 34:804–08; and Sivolapenko et al., 1995, Lancet 346:1662–1666). At the time of the invention, it was believed that such false positive tests result in surgical dissections that will not benefit the patient, but instead, will increase morbidity. Therefore, false positive tests "should be diligently avoided in the surgical patient" (Stephens et al., 1993, supra). For example, since false positive lymph nodes are not easily examined by palpation, such false positives are currently viewed as presenting a serious problem to general applicability of radioimmunodiagnosis and radioimmunoguided surgery (Stephens et al., 1993, supra).

False positive ("false tumor-positive") lymph nodes (LN) have been characterized as germinal center staining for noncellular tumor antigen; and classified as type III: RIGS positive, histology (hematoxylin and eosin) negative for tumor. It is estimated that of the lymph nodes detected by RAIDS or RIGS, 80% are false positive (i.e., lack evident tumor cells but contain noncellular tumor antigen). Several mechanisms to explain such false positives have been proposed. One suggested mechanism is that shed tumor antigen causes an inflammatory process mediated by the tumor antigen/antibody complex that may also involve a T cell-mediated cytotoxic response (Stephens et al., 1993, supra). Alternately, tumor antigen is retained in the form of antigen/antibody complexes, attached to follicular dendritic cells located in the germinal centers (Cornelius and West, 1996, supra). In another proposed scenario, tumor antigen detected is primarily in sinusoidal macrophage as part of antigen processing (Cornelius and West, 1996, supra). The phenomenon of false positives is problematic, and needs to be further investigated to identify its origin and to explain its relationship, if any, to treatment options, and resultant clinical outcomes following treatment, for the affected patient.

3. Need for New Therapeutic Approaches

While new therapeutics are being developed and tested for efficacy, many of the currently available cancer treatments are relatively ineffective. It has been reported that chemotherapy results in a durable response in only 4% of treated patients, and substantially prolongs the life of only an additional 3% of patients with advanced cancer (Smith et al., 1993, J. Natl. Cancer Inst. 85:1460–1474). Current treatments for metastases are both cost-prohibitive, relatively ineffective, and present with major toxicity. Regarding the latter and depending on the drug or drug combination used, systemic chemotherapy may result in one or more toxicities including hematologic, vascular, neural, gastrointestinal, renal, pulmonary, otologic, and lethal.

Surgery, when possible, is used as a standard therapy for patients with isolated metastases (e.g., hepatic and/or pulmonary). After resection, the projected five year survival rate may range from 25–35%, the mean survival is about 31 months, and the 30-day mortality rate is about 4% (Wade, 1996, *J. Am. Coll. Surg.* 182:353–361). However, about 25% to 45% of patients who have had resection of their colorectal cancer later develop recurrences (Zaveidsky et al., 1994, supra). Thus, there continues to be a need for identifying processes which enhance tumor growth and metastasis. More particularly, there remains a need for a method of detecting and treating processes that contribute to tumor development at an early stage (e.g., Stage I or II) or late stage (e.g., Stage III or IV) before, during, or after surgical resection of tumor. Likewise, there remains a need for a method of detecting and treating precancerous conditions (e.g., prior to, or at an early stage of, development of primary tumor or regrowth).

SUMMARY OF THE INVENTION

Accordingly, it is a primary object of the present invention to provide compositions that may be used to detect mucin or other shed tumor antigens containing Tn antigen in a method for detecting a pro-tumor immune response in an individual.

It is a further object of the present invention to provide compositions that may be used to detect localized shed tumor antigen in lymphoid tissues involved in a pro-tumor immune response, wherein lymphoid tissues detected as containing shed tumor antigen are then surgically removed from the individual being treated.

It is also a further object of the present invention to provide compositions which can be used to detect lymphoid tissues involved in a pro-tumor immune response, wherein such detection is a prognostic indicator that invasion and metastasis has occurred, or is likely to occur, from the local primary tumor.

The foregoing objects are achieved by identifying a novel mechanism in which mucin and mucin-like molecules, shed from tumor cells of solid, nonlymphoid tumors, are capable of inducing an immune response which promotes tumor growth and metastasis, as will be more apparent from the following description. This mechanism of tumor promotion involves the specific type of immune response induced by shed tumor antigen (mucin and mucin-like molecules containing Tn antigen). This specific immune response, a "pro-tumor immune response", can involve (a) the contact or presence of shed tumor antigen in relation to the cell surface of B cells, and cell surface of follicular dendritic cells or other antigen presenting cells (e.g., contained in lymphoid tissues); (b) activation of such B cells to proliferate, (c) and differentiation of the activated B cells into plasma cells which secrete anti-shed tumor antigen antibody that forms complexes with shed tumor antigen in sufficient amounts which may act indirectly (via immune effector cells) and/or directly (on the tumor cells) to mediate tumor progression. Continuous presentation of immune complexes containing shed tumor antigen by FDC plays an important role in the persistence of a pro-tumor immune response.

In one embodiment of the present invention, a composition having binding specificity for shed tumor antigen is used to find and bind to shed tumor antigen localized in lymphoid tissues in an individual. The lymphoid tissue containing shed tumor antigen may then be surgically excised from the individual, thereby immuno-modulating the immune system to prevent the tumor promoting function of the pro-tumor immune response.

DETAILED DESCRIPTION OF THE PREFERRED EMBODIMENTS

Definitions

Figure 1:
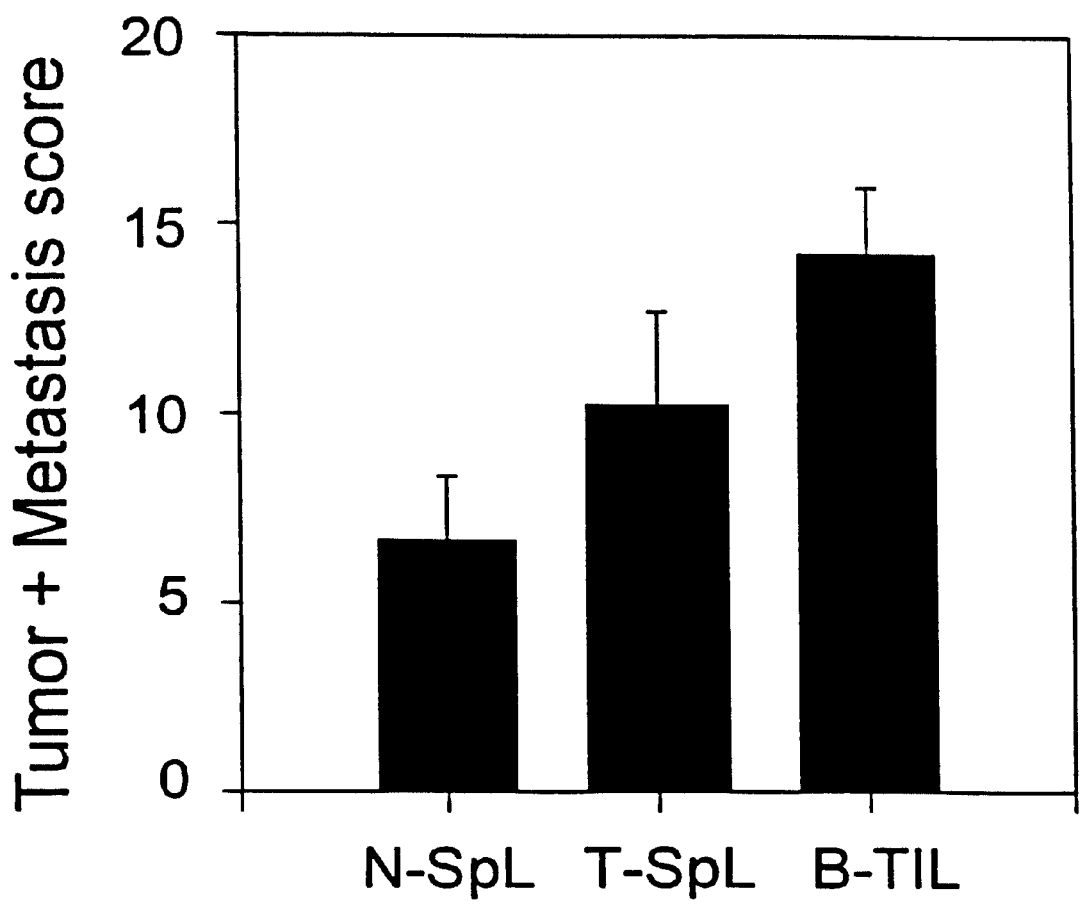
FIG. 1 is a bar graph illustrating in vivo spleen tumor cell growth and liver metastasis (combined score) in the presence of lymphoid tissue B lymphocytes from tumor bearing mice (T-SpL), B lymphocytes from tumor (B-TIL), and splenic B lymphocytes from normal mice (N-Spl).

The term "lymphoid tissue" is used herein, for purposes of the specification and claims, to mean a tissue which contains localized areas of antigen presenting cells (e.g., follicular or germinal center dendritic cells) and B cells; and which contains infiltrates ("deposits") of shed tumor antigen as detected by an administered detector molecule. An example of such localized areas comprises germinal centers. Such lymphoid tissues comprise lymphatic tissues that may include, but are not limited to, lymph nodes; milky patches in the mesenterium of the intestine; momentum; appendix; Peyer's patches; loose connective tissue (e.g., associated with vessels in the walls of the aorta); lymphatic vessels; submucosal spaces; subserosa spaces; peritoneal cavity; ligaments (e.g., gastrohepatic ligament); and epineura.

The term "B cells" is used herein, for purposes of the specification and claims, to mean mammalian (and preferably human) nonmalignant B cells. As known to those skilled in the art, malignant B cells refers to cancer cells of B cell origin, such as B cell lymphomas, and B cell leukemias. Thus, the term "B cells", as used herein in reference to a pro-tumor immune response, specifically excludes B cell lymphomas, B cell leukemias, and cancer cells of B cell origin. In that regard, nonmalignant B cells are inclusive of one or more of memory B cells; mature B cells; and a subpopulation thereof comprising shed tumor antigen-stimulated B cells which have a cell surface-bound immunoglobulin comprising antibody against shed tumor antigen, and which can be induced to proliferate and differentiate into plasma cells which produce/secrete anti-shed tumor antigen antibody that may contribute to a promotion of tumor progression, as will be more apparent from the following embodiments.

The term "solid, non-lymphoid tumor" is used herein, for purposes of the specification and claims, to mean any primary tumor (a) of ductal epithelial cell origin, including tumors originating in the liver, lung, brain, bone marrow, adrenal gland, breast, colon, pancreas, stomach, prostate, gastrointestinal tract, or reproductive tract (cervix, ovaries, endometrium etc.); and (b) which secretes or produces shed tumor antigen (e.g., serous, or endometroid, or mucinous tumors). For the purposes of the present invention, "solid, non-lymphoid tumor" may also include melanoma.

The term "detector molecule" is used herein, for purposes of the specification and claims, to mean a peptide having binding specificity for the Tn antigen present on a shed tumor antigen, wherein the peptide is bound to a detectable label such as a radioisotope or a magnetic molecule using covalent or noncovalent means. The presence of the detector molecule can be detected and localized using an instrument or probe, as will be more apparent from the following embodiments. Preferred radioisotopes are those that emit a relatively weak gamma emission (e.g., 25–300 keV) that is detected efficiently by the instrument or probe used for detection; may be attenuated by soft tissue, thereby resulting in minimal in vivo scatter from tissue surrounding the radioactive tissue; and having a half life which permits waiting the time period necessary to establish a background level (blood circulation reduction) of radio-activity in the individual being treated. Such radio-isotopes are known in the art to include, but are not limited to, $^{125}$I, $^{111}$In, $^{57}$Co, $^{99m}$Tc, and $^{75}$Se. An "effective amount of detector molecule" is used herein, for purposes of the specification and claims, to mean a sufficient amount of the detector molecule, which after blood circulation reduction, is able to localize and concentrate in lymphoid tissues containing shed tumor antigen so as to be detected by the means for detecting the signal emitted by the concentrated detector molecule, as will be more apparent from the following embodiments.

The term "peptide" is used herein, for purposes of the specification and claims, to mean a molecule having at least about 10 and at most about 116 amino acid residues, wherein the amino acid residues are a contiguous sequence of amino acid residues of SEQ ID NO:1; wherein the contiguous sequence of amino acid residues form a binding region having binding specificity for the Tn antigen, but lacking detectable binding specificity for the sTn antigen; and wherein the peptide can bind Tn antigen of shed tumor antigen or similar Tn antigen-containing glycoproteins (e.g., asialo-bovine salivary mucin). Thus, the peptide may consist of an amino acid sequence (the 116 amino acid residues) of SEQ ID NO:1, or may consist of a portion thereof (at least about 10 and at most about 115 amino acid residues, wherein the amino acid residues are a contiguous sequence of amino acid residues of SEQ ID NO:1; and wherein the contiguous sequence of amino acid residues form a binding region having binding specificity for the Tn antigen, but lacking detectable binding specificity for the sTn antigen (e.g., by an immunoassay)). The peptide may be derived from the amino acid sequence of SEQ ID NO:1, and may be synthesized or recombinantly produced. "Binding specificity" means that the peptide (or detector molecule comprising the peptide) recognizes and binds specifically (vs. nonspecifically) to Tn antigen of shed tumor antigen, and minimally (if at all) to the surface of normal human (nonmalignant or non-precancerous or noncryptic) cells/tissue, such that the binding specificity allows for differential detection of shed tumor antigen over normal cells/tissue. In a preferred embodiment, an "effective amount" of the peptide has binding specificity (e.g., and with a binding affinity) sufficient to recognize and bind to shed tumor antigen in vivo in individuals having a pro-tumor immune response. In a preferred embodiment, binding affinities found to be suitable for in vivo applications may include binding affinities ranging from $2 \times 10^3$ M to $3 \times 10^9$ M or greater. A peptide, which exemplifies a peptide which may be used to form a detector molecule according to the present invention, has the amino acid sequence of SEQ ID NO:1, or is a peptide comprising a portion thereof (has less than the 116 amino acids of SEQ ID NO:1, but is derived from the amino acid sequence of SEQ ID NO:1; e.g., SEQ ID NOs: 2–6); and binds to a Tn antigen expressing-shed tumor antigen comprising mucin or mucin-like molecules. Other peptides, that bind to tumor-derive mucin and that have been shown to be safely administered to humans, have been described previously, and include a sFv of mAb CC49 (binding comprising sTn antigen; Milenic et al., 1991, *Cancer Res.* 51:6363–6371, and Larson et al., 1997, *Cancer* 80S:2458–2468); and αM2 (binding comprising peptide epitope; Sivolapenko et al., 1995, *Lancet,* 346:1662–1666).

"Consisting of", in relation to amino acid sequence of a peptide described herein, is a term used hereinafter for the purposes of the specification and claims to refer to a conservative substitution or modification of one or more amino acids in that sequence such that the tertiary configuration and Tn binding specificity of the peptide is substantially unchanged. "Conservative substitutions" is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. Such conservative substitutions would not be expected to substantially alter the biological activity of the peptide such that it can no longer be used to bind to and detect shed tumor antigen in vivo or in vitro. "Modification", in relation to amino acid sequence of a peptide, is defined functionally as a deletion of or addition of one or more amino acids which does not impart a substantial change in the biological activity (binding to shed tumor antigen) or specificity of the peptide such that it can no longer be used to bind to and detect shed tumor antigen in vivo. In particular, a peptide according to the present invention may be modified, using methods known by those skilled in the art, by adding one or more amino acids or functional groups for one or more properties which include, but are not limited to, facilitating the labeling of the peptide with a radioisotope or magnetic molecule (e.g., cysteine and tyrosine facilitate radiolabeling); to achieve favorable kinetics (rapid bioclearance, while maintaining sufficient localization and retention of the detector molecule to allow for detection and removal of lymphoid tissues containing shed tumor antigen; to alter the immunogenicity of the peptide, if any; and to minimize toxicity, if any.

The term "metastases" or "metastatic tumor cell" is used herein, for purposes of the specification and claims, to mean a metastasis from a primary tumor wherein the primary tumor is a solid, non-lymphoid tumor, as will be more apparent from the following embodiments.

The term "shed tumor antigen" is used herein, for purposes of the specification and claims, to mean a mucin or mucin-like glycoprotein which:

(a) has a molecular size equal to or greater than about 100 kilodaltons;

(b) is released (e.g., shed) from a primary tumor or its metastases, thereby becoming soluble and allowing movement into lymphoid tissues regional or distal to the primary tumor or its metastases;

(c) comprises an polyvalent antigen which has repeated subunits (e.g., peptide domain and/or repeated carbohydrate chains), each subunit containing one or more epitopes available for binding to a peptide, wherein at least one epitope comprises the Tn antigen;

(d) is produced by tumor cells in an underglycosylated (incompletely glycosylated) form and/or in a form of altered glycosylation as compared to the glycosylation pattern of the same molecule typically found exposed on most normal (nonmalignant or non-precancerous) cells;

(e) is capable of inducing a humoral immune response resulting in the production and secretion of anti-shed tumor antigen antibody; and (f) can interact with anti-shed tumor antigen antibody in forming immune complexes, wherein the immune complexes may bind and cross-link Fc receptors (e.g., FcγRI) present on the surface of Fcreceptor-expressing cells.

With regard to the tumor antigen being soluble, the tumor antigen is noncellular ("shed") tumor antigen. Non-cellular tumor antigen comprises soluble tumor antigen that is not an integral part of a living tumor cell. Such shed tumor antigen exists in a form selected from the group consisting of free form (shed tumor antigen alone), in an immune complex form (shed tumor antigen bound to anti-shed tumor antigen antibody), in a form as presented on the surface of follicular dendritic cells (antigen presenting cells), in a form as bound to the cell surface of B cells, and as a form in tumor cell membranes existing apart from living tumor cells (i.e., soluble membrane complexes representing portions of dead tumor cells).

For a review of the structure of the family of mucin molecules, see Finn et al. (1995, *Immunol. Rev.,* 145:62–89). Briefly, mucins are high molecular weight glycoproteins (e.g., greater than about 100 kiloDaltons (kD) in molecular mass) of which a significant portion of the polypeptide backbone comprises a domain composed of a tandomly repeating peptide subunits (e.g. about 20 to about 125 repeats). Mucins are found on normal ductal epithelial cells in sequestered locations that are not normally exposed to the immune system (e.g., restricted to the lumen of duct). However, in processes such as transformation (e.g, pre-cancerous) or tumor development, and due to various factors (e.g., the increased production of mucin, lack of availability of glycosyltransferases), tumor cells produce mucin in an underglycosylated (incompletely glycosylated) form and/or in a form of altered glycosylation (e.g., with an exposed Tn antigen, or with a terminal sialic acid). An immune response against tumor cell-produced mucin is thought to be primarily directed against one or more epitopes on the mucin glycoprotein which is exposed to the immune system as a result of underglycosylation or altered glycosylation. Thus, because of the underglycosylation or altered glycosylation in growing tumors, the shed tumor mucin has epitopes not normally found on mucin or not normally exposed to the immune system. Such epitopes may include, but are not limited to, carbohydrate epitopes comprising the sialyl Tn (sTn) antigen (substantially comprising the NeuAc portion of NeuAcα2→6GalNAcα1→O-Ser- or Thr); the Tn antigen (comprising the GalNAc portion of GalNAcα1→O-Ser- or Thr), the T antigen, or other sialic acid containing epitopes (e.g., substantially comprising NeuAc α2 on the carbohydrate chains (a) NeuAcα2→6Gal→O-Ser- or Thr, (b) NeuAcα2→3Gal→O-Ser- or (c) NeuAcα2→3GalNAc→O-Ser- or Thr); or a combination thereof (e.g., comprising both the sTn antigen and Tn antigen). An example of a mucin-like glycoprotein which is differentially glycosylated by tumor cells, and is shed by tumor cells, is SSEA-1 antigen.

Tumor-associated glycoproteins, and their characterization such as nature of carbohydrate chain structure and/or monoclonal antibody binding, are known to those skilled in the art (see, e.g., Table V of Hakomori, 1989, *Adv. Cancer Res.* 52:257–331). Tumor-associated glycoproteins which are known to those skilled in the art as being found in a soluble form include, but are not limited, to the human equivalents of those presented in Table 1.

TABLE 1

| Soluble-tumor Ag | Antibody | Characteristic |
|---|---|---|
| sialyl SSEA-1 ("SLX")[1] | FH-6 | pancreatic, lung gastric, ovarian, cervical adenocarcinomas |
| PA8-15[2] | mAb PA8-15 | pancreatic, gastrointestinal carcinoma |
| MUSE 11[3] | mAb MUSE 11 | adenocarcinoma pancreatic cancer |
| Her-2/neu[4] | mAb GFD-OA-p185-1 | 185 kD; various carcinomas |
| TA90[5] or U-TAA[5] | mAb ADI-40F4 | melanoma |
| KL-6 antigen[6] | mAb Kl-6 | various adenocarcinomas |

[1]Lee et al., 1992 J. Formos. Med. Assoc. 91:760–3.
[2]Arai et al., 1990, Jpn. J. Clin. Oncol. 20:145–53.
[3]Takai et al., 1991, Nippon Shokakibyo Gakkai Zasshi, 88:170–4.
[4]Meden and Kuhn, 1997, Eur. J. Obstet. Gynecol. Reprod. Biol. 71:173–9.
[5]Hsueh et al., 1998, J. Clin. Oncol. 16:2913–2920; Euhus et al., 1990, Int. J. Cancer 45:1065–70.
[6]Kohno et al., 1989, Cancer Res. 49:3412–9.

For purposes of illustration, and not limitation, in a preferred embodiment of the present invention, the shed tumor antigen comprises the gene product of the MUC-1 gene (also known as polymorphic epithelial mucin) as detected by the epitope comprising the Tn antigen.

With regard to the humoral immune response that may be induced by the shed tumor antigen, it is known that the immune response induced by tumor cell-associated mucin is predominantly cellular (CD8+), with little or no antibody produced. In contrast to mucin bound to the surface of whole tumor cells, shed tumor mucin induces a humoral immune response that eventually results in antibody production, but not cytotoxic T cell responses (Apostolopoulos et al., 1994, *Cancer Res.* 54:5186). However, it was not known that such an immune response may promote tumor cell growth and metastasis. In that regard, it appears that shed tumor antigen may be an immunodominant tumor antigen as compared with cell-associated antigens of the tumor presented to the immune system in the process of tumorigenesis. More particularly, shed tumor antigen may induce a humoral response, the eventual result of which may be that a significant amount of the antibody response is produced against the shed tumor antigen, relative to that induced against any other single tumor cell-associated antigen ("dominant" response). The result of this specific type of immune response is a form of tolerization of the immune system to some tumor antigens other than shed tumor antigen; and hence, the inhibition of the development of an effective antitumor humoral immune response.

The term "individual" is used herein, for purposes of the specification and claims, to mean a mammal; and preferably a human; particularly an individual who is at risk of developing, or has developed, a pro-tumor immune response. An individual who is at risk of developing, or has developed, a pro-tumor immune response may include an individual having a primary tumor comprising a solid, non-lymphoid tumor and/or its metastases; an individual with a pre-cancerous condition comprising transformed (abnormal in proliferation and/or genetic makeup as compared to normal epithelial cells of the same type) cells of ductal epithelial origin which release shed tumor antigen; an individual who is at high risk (e.g., environmentally and/or genetically) for developing a solid, non-lymphoid tumor; or an individual who has been treated for a solid, nonlymphoid tumor and thereby inherently carries a risk of recurrence. In one embodiment, a detector molecule comprising a peptide according to the present invention is intended for use to detect lymphoid tissues containing shed tumor antigen and that are involved in a pro-tumor immune response in an individual who is at risk for developing, or who has developed, solid nonlymphoid tumor.

The term "tumor promoting factor" is used herein, for purposes of the specification and claims, to anti-shed tumor antigen antibody secreted by plasma cells, which as an IgG, binds to shed tumor antigen in forming immune complexes, wherein the immune complexes may act: on host cells which are mediators of inflammation and/or angiogenesis (e.g., granulocytes, and/or macrophages, and/or vascular endothelial cells); and/or directly (acting on the tumor cell itself) to mediate tumor progression including, but not limited to, promoting tumor growth and/or metastasis, and/or advancing stage of malignancy. Such immune complexes may also: induce a cascade of inflammatory processes which promote tumor development; downregulate T helper cells which normally may mount an immune response against tumor cell-associated antigens, thereby inhibiting development of an antitumor immune response; inhibit tumor cell-associated antigen presentation to human tumor-specific cytotoxic lymphocytes; increase expression on primary tumor cells of cell-surface molecules which promote metastasis; cross-link Fc gamma receptors on tumor cells which may induce tumor proliferation (e.g., possibly by activating tyrosine kinase production) and/or an increase in tumor production and secretion of mucin; facilitate a local environment which mediates spread and/or development of metastases beyond the primary tumor and to lymphoid tissues regional or distal to the primary tumor; and interact with and bind to endothelial cells in promoting angiogenesis.

The term "pro-tumor immune response" is used herein, for purposes of the specification and claims, to mean an immune response induced by shed tumor antigen, wherein the immune response can promote tumor growth and metastasis. The pro-tumor immune response may involve (a) the contact or presence of shed tumor antigen in relation to the cell surface of B cells, and cell surface of follicular dendritic cells or other antigen presenting cells (e.g., contained in lymphoid tissues); (b) activation of such B cells by shed tumor antigen; and (c) differentiation of activated B cells into plasma cells which secrete tumor promoting factor in sufficient amounts that may act indirectly (via immune effector cells) and/or directly (on the tumor cells) to mediate tumor progression (e.g., invasion and metastasis). Typically, foci of a pro-tumor immune response may be localized to lymphoid tissues containing shed-tumor antigen activated B cells, shed tumor antigen, and follicular dendritic cells presenting shed tumor antigen (e.g., in the form of immune complexes).

One drawback of using either radioimmunodiagnosis (RAIDS) or radioimmunoguided surgery (RIGS) to search for metastases from solid, nonlymphoid tumors is the observed false positivity (lack of demonstration of tumor cells) in draining lymph nodes. Current belief is that surgical removal of such lymph nodes presents a serious problem to general applicability of radioimmunodiagnosis and radioimmunoguided surgery since the dissection represents removal of non-neoplastic tissue (see, e.g., Stephens et al., 1993, supra). Another drawback is that radioimmunodiagnosis and radioimmunoguided surgery typically use an antibody for targeting the imaging agent to the tumor. Such antibody, when having specificity for shed tumor antigen, may cause the formation of additional immune complexes which could potentially aid tumor progression. The present invention relates to the discovery of a novel mechanism in which shed tumor antigen induces a pro-tumor immune response which can mediate tumor progression. This mechanism involves the specific type of immune response induced by shed tumor antigen. Foci of the immune cells and shed tumor antigen involved in the pro-tumor immune response are often found in lymphoid tissues wherein the detection of these involved lymphoid tissues represents some of the false positive lymph nodes described for radioimmunodiagnosis and radioimmunoguided surgery. In a preferred embodiment of the invention, provided are peptides having binding specificity for the Tn antigen which may be used to form detector molecules for detecting lymphoid tissues involved in a pro-tumor immune response. Peptides have one or more advantages over antibodies, wherein the one or more advantages may be selected from the group consisting of reduced immunogenicity, an increased rate of bioclearance (e.g., blood pool reduction), and an unexpected advantage of lacking an Fc domain, as will be more apparent from the following descriptions.

A peptide, and particularly a detector molecule comprised of a peptide, of the present invention relates to use in detecting the presence of shed tumor antigen in lymphoid tissues involved in a pro-tumor immune response in an individual. Optionally, the individual may then be therapeutically treated by surgically removing those lymphoid tissues detected; i.e., all of the detected lymphoid tissue, or that portion of the lymphoid tissue containing shed tumor antigen, may be surgically resected. By surgically resecting the lymphoid tissue, removed from the individual is one or more of localized: shed tumor antigen; shed tumor antigen-activated B cells; and follicular dendritic cells presenting shed tumor antigen. A therapeutic effect resulting from surgically resecting such lymphoid tissue (e.g., false positive lymph nodes) would be an unexpected result, as the current view is that such surgical resections do not benefit the patient, but instead increases morbidity (Stephens et al., 1993, supra). Additionally, a therapeutic effect resulting from surgically resecting lymph nodes regional to a primary tumor to prevent tumor growth and progression is an unexpected result in view of the belief by those skilled in the art that regional lymph nodes play an important role in the development of tumor immunity (Fisher and Fisher, 1971, *Cancer,* 27:1001–04); and that regional lymph nodes are of primary importance in the maintenance of tumor immunity (Fisher and Fisher, 1972, *Cancer,* 29:1496–1501).

The present invention also comprises peptides which may be used to form detector molecules that may be utilized to detect a specific type of immune response or process ("pro-tumor immune response") in an individual, wherein this specific type of immune response promotes tumor development and progression as will be more apparent from the following illustrative embodiments. In a preferred embodiment, the shed tumor antigen is mucin-1 (polymorphic epithelial mucin), or a shed tumor antigen other than mucin but which also contains the Tn antigen. In one illustration of the present invention, an effective amount of peptide comprises an amino acid sequence consisting of SEQ ID NO:1, or a portion thereof having binding specificity for the Tn antigen, is used in a method for detecting the presence or absence of a pro-tumor immune response. The peptide is used to form an effective amount of detector molecule, having binding specificity for shed tumor antigen, and is administered to the individual to be treated. As appreciated by those skilled in the art, an effective amount of detector molecule will vary depending on such factors which include, but are not limited to, the type and nature of detector molecule label used (e.g., a radioisotope, and the emission of the isotope; the size, type, and strength of emission from, a magnetic molecule), the efficiency of attaching the affinity molecule to the detectable label in forming a detector molecule, the binding specificity and affinity of the detector molecule for shed tumor antigen, and the efficiency of the individual's bioclearance of the detector molecule (e.g., blood circulation reduction). For purposes of illustration, and not limitation, a minimum detectable radioactive signal from detector molecule containing $^{125}I$ is approximately 10 counts/second; and a minimum amount of radioactivity detectable when scanning continuously is approximately 3 nanoCuries (nCi). After administration of the detector molecule, the individual is then subjected to a time interval sufficient for allowing the detector molecule to localize and concentrate in lymphoid tissue containing shed tumor antigen, and also allowing for unbound detector molecule (e.g., detector molecule not specifically bound to shed tumor antigen) to clear from the individual's system (e.g., blood circulation reduction) thereby achieving a background level of signal emitting or resonating from non-specifically bound detector molecule. In general, and depending on the detector molecule used, a time period could vary from hours up to two weeks after administration of the detector molecule to achieve sufficient clearance of radioactivity from the blood circulation when using a detector molecule which is radiolabeled. However, as appreciated by those skilled in the art, such a time period may be shorter or longer depending on several parameters including, but not limited to, circulating immune complex formation, kinetics of tumor antigen shedding, chemical properties (e.g., solubility, hydrophobicity, etc.) of the affinity molecule utilized in making the detector molecule, and clearance properties of the detector molecule. After such a time period, the individual to whom is administered is then accessed by exploratory surgery, and probed or scanned for identifying and localizing lymphoid tissues containing shed tumor antigen by using an instrument or probe capable of distinguishing and localizing the signal from the detector molecule bound to shed tumor antigen. The instrument or probe is positioned adjacent to the lymphoid tissue, wherein if shed tumor antigen is detectably present in that lymphoid tissue, a signal of measurably greater intensity or strength than that of the background level is detected. The finding of lymphoid tissue detected as containing shed tumor antigen is an indicator of the presence of a pro-tumor immune response in the individual. In a method of immune corrective surgery, the same procedure is followed (for detecting lymphoid tissue containing shed tumor antigen), but the method of immune corrective surgery further includes surgically resecting all or that portion of the lymphoid tissue detected as containing shed tumor antigen. The same area from which the lymphoid tissue was removed may be rescanned using the probe to confirm that the lymphoid tissue detected as containing shed tumor antigen has been completely removed, or alternatively, that a second source of lymphoid tissue, located directly below the space from which was removed the initial lymphoid tissue, is not the source for all or a portion of the detected signal (representing the presence of shed tumor antigen). Thus, the rescanning ensures that all lymphoid tissue detected by the probe or instrument as containing shed tumor antigen, and which exhibits a signal of measurably greater intensity or strength than that of the background level, may be detected and then surgically removed. For purposes of illustration, a "signal of measurably greater intensity of strength than that of the background level" is a signal greater or equal to the background signal plus 3 standard deviations.

For purposes of the description, the compositions of the present invention, and some of their uses, will be illustrated in the following examples.

EXAMPLE 1

This example, and other Examples herein, provide evidence of the B cell involvement, and the specific type of immune response to shed tumor antigen in lymphoid tissues, which are involved in a pro-tumor immune response that promotes tumor progression and metastasis. For this Example, and Examples 2 and 3, it is important to consider the following concept. Various strains of mice were used as a standard animal model for evaluating whether a germinal center B cell response may be involved in tumor progression, including promoting metastasis. In the tumor bearing mice of B cell competent strains, a similar germinal center B cell response was observed in lymph nodes regional to a primary tumor as observed in tumor bearing humans. In that regard, and to assess whether B cells are effector cells of, at least in part, a tumor promoting immune response, an in vivo standard experimental model was used. To determine whether different populations of B lymphocytes could influence tumor progression in vivo, C3H mice were injected in the mammary pad with $1 \times 10^6$ Met 129 (high mucin-secreting mammary tumor) cells. Tumor growth in CH3 mammary gland tumor-bearing mice was compared when the mice were injected every 2 days for a 14 day period with either B lymphocytes (50,000 cells) isolated from normal mouse spleen, B lymphocytes isolated from lymphoid tissues (e.g., spleens) of tumor bearing mice (50,000 cells), or 50,000 B lymphocytes isolated from tumor tissue (B-TIL) of tumor bearing mice. The various B cell populations were isolated using magnetic beads having anti-CD19 mAb bound thereto. After the 14 day period, liver metastasis and spleen tumor growth (tumor+metastasis score) was evaluated. As shown in FIG. 1, B lymphocytes from lymphoid tissue of tumor bearing mice ("T-Spl") and B-TIL each promoted statistically significant tumor growth and metastasis in vivo, whereas B lymphocytes from normal spleen ("N-Spl") did not enhance either tumor growth or metastasis. A conclusion that can be drawn from these results is that to gain the ability to promote tumor progression, B lymphocytes contained in lymphoid tissues must first be exposed to shed tumor antigen.

Figure 2:
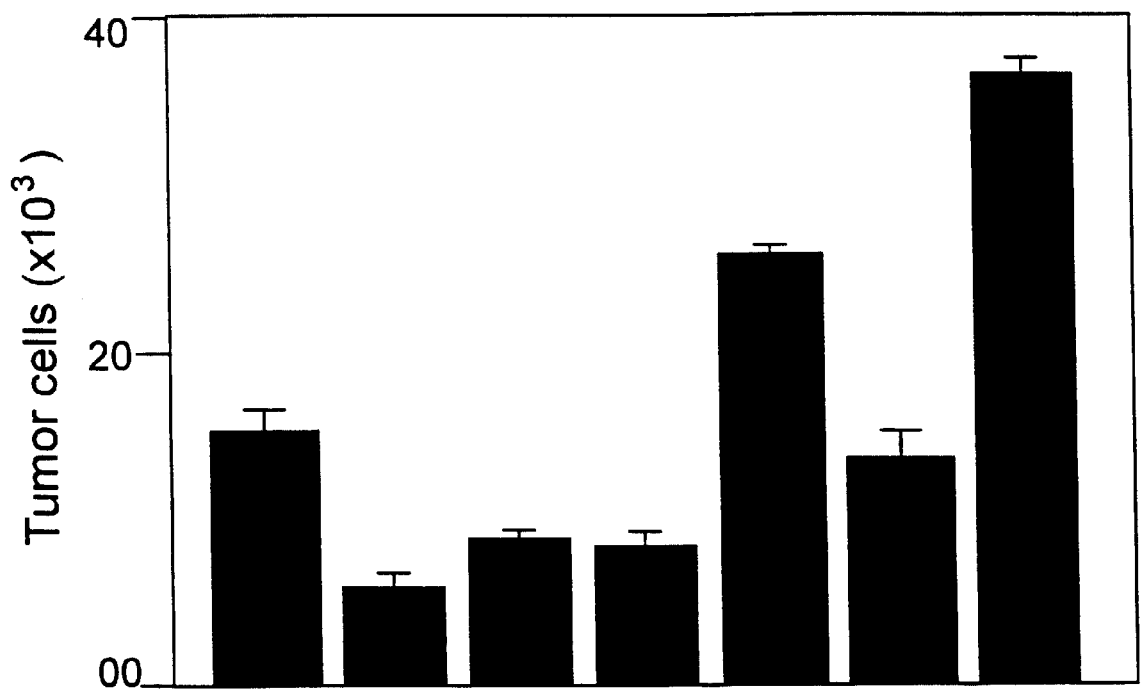
FIG. 2 is a bar graph illustrating in vitro tumor growth of Met 129 tumor cells alone; or co-incubated with either CD8+ cells, CD4+ cells, CD8+ cells and CD4+ cells, B cells from tumor bearing mice ("B"), CD8+ cells and B, or B and CD8+ cells and CD4+ cells.

The following experiment illustrates that B cell promotion of tumor progression in vitro can be mediated via a direct action by B cells that does not require a T cell intermediary response; but may also act synergistically with CD4+ T cells, when present. In this illustration, several populations of lymphocytes were isolated using magnetic bead separation techniques from Met 129 tumors removed from C3H mice. The lymphocyte populations included B cells isolated from tumor bearing mice, CD4+ lymphocytes isolated from tumor bearing mice, and CD8+ lymphocytes isolated from tumor bearing mice (CD8+). Ten thousand Met 129 cells were cultured in 1.5 ml of tissue culture medium supplemented with 10% fetal bovine serum (FBS) per well in 24 well plates alone, or in the presence of either 10,000 CD8+ cells, in the presence of 10,000 CD4+ cells, in the presence of 10,000 CD8+ cells and 10,000 CD4+ cells, in the presence of 10,000 B cells, in the presence of 10,000 B cells and 10,000 CD8+ cells, or in the presence of 10,000 CD8+ cells, 10,000 CD4+ cells and 10,000 B cells. After 72 hours of co-incubation in monolayer culture, Met 129 tumor cell growth was quantitated using Alcian blue staining; e.g., adherent mucin-producing cells (Met 129 tumor cells) were counted. As shown in FIG. 2, CD8+ cells co-incubated with Met 129 (Met 129+, CD8++, CD4+−, B−) resulted in a statistically significant reduction in tumor cell growth, and thus appeared to effect Met 129 tumor cell death when compared to the control of Met 129 alone (Met 129+, CD8+−, CD4+−, B−) Likewise, a slight reduction in tumor growth or no increase in tumor growth, as compared to the control, was observed when Met 129 tumor cells were co-incubated with either CD4+ cells (Met 129+, CD8+−, CD4++, B−), in the presence of CD8+ cells and CD4+ cells (Met 129+, CD8++, CD4++, B−), or in the presence of B cells and CD8+ cells (Met 129+, CD8++, CD4+−, B+). In contrast, statistically significant increased tumor cell growth was observed when B cells were co-incubated with Met 129 tumor cells (FIG. 2: Met 129+, CD8+−, CD4+−, B+), and when CD8+ cells, CD4+ cells and B cells were co-incubated with Met 129 tumor cells (FIG. 2: Met 129+, CD8++, CD4++, B+), as compared to growth of the control of Met 129 tumor cells alone (Met 129+, CD8+−, CD4+−, B−).

In summary, these results indicate that B cells alone can promote tumor progression via a direct action by B cells that does not require a T cell intermediary response (FIG. 2: Met 129+, CD8+−, CD4+−, B+).

EXAMPLE 2

In this illustration, shown is that a process that depletes B cells can also affect tumor progression in tumor bearing animals. Fifty three C3H mice were injected intrasplenically with $10^6$ Met 129 tumor cells. The injected mice were then divided into two treatment groups. One group of 28 mice was injected with an irrelevant (not directed against any specific mouse antigen) goat IgG antibody (170 μg per injection) at days 5, 7, and 9 following tumor challenge. A second group consisted of 25 mice injected with goat anti-mouse IgG and goat anti-mouse IgM (170 μg per injection) at days 5, 7, and 9 following tumor challenge. The goat anti-mouse IgG and IgM was used to deplete the C3H mice of their B cells, thereby interrupting the host B cell-mediated pro-tumor immune response. At 22 days following tumor challenge, the two groups of mice were analyzed for primary tumor growth in the spleen, metastasis to the liver, and extra-regional metastasis (abdominal lymph nodes). Table 2 shows one experiment in which compared was primary tumor growth, and the incidence of liver metastasis ("Liver Met.") and extra-regional metastasis ("Extra-R Met.") in the mice treated with irrelevant goat IgG ("Goat-IgG"), and mice treated with goat anti-mouse IgG and goat anti-mouse IgM ("Anti-IgG Anti-IgM"). Table 2 shows that there is a statistically significant reduction in the incidence of metastasis in B cell-depleted mice ("Anti-IgG Anti-IgM") as compared to the control group receiving irrelevant IgG.

TABLE 2

| Observed | Goat-IgG Control | Anti-IgG Anti-IgM |
|---|---|---|
| Tumor | 8 of 8 | 6 of 6 |
| Liver Met. | 5 of 8 | 0 of 6 |
| Extra-R Met. | 6 of 8 | 0 of 6 |

Figure 3:
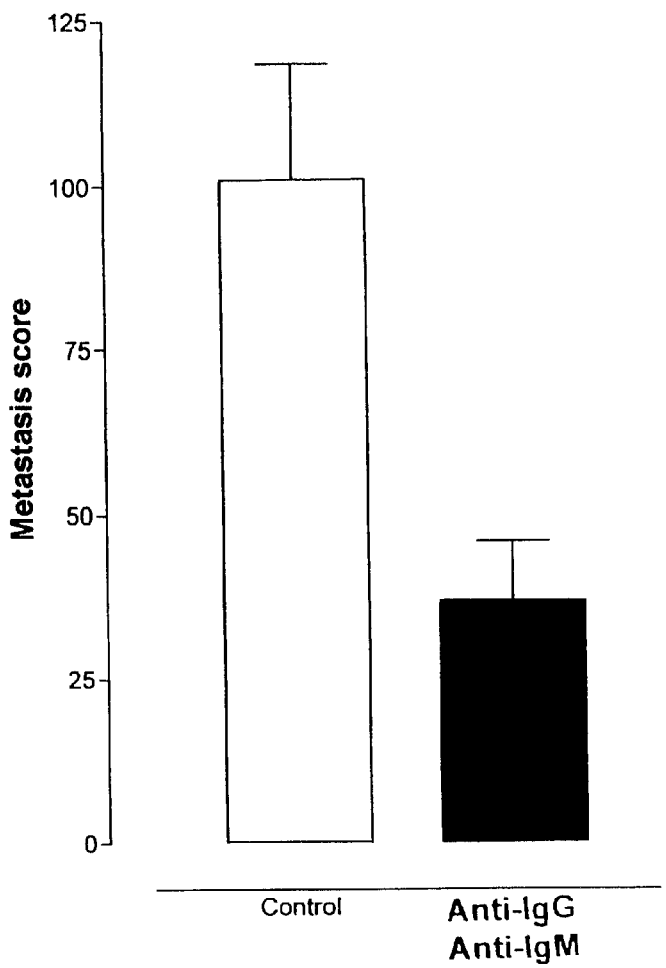
FIG. 3 is a bar graph illustrating the extra-regional (lymph node) and liver metastases scores (combined as "metastasis score") in mice treated with either irrelevant goat IgG, or in mice having B cells depleted ("Anti-IgG").

Spleen tumor was scored and compared among the two groups of mice. Treatment of the tumor bearing mice with either goat IgG, or goat anti-mouse IgG and goat anti-mouse IgM, had little effect on the growth of the primary tumor in the spleens. In contrast, as shown in FIG. 3, mice in which B cells were depleted ("Anti-IgG") showed a statistically significant reduction in the incidence of extra-regional metastasis and liver metastasis as compared to the extra-regional metastasis and liver metastasis exhibited by the control group of mice treated with irrelevant goat IgG. The results in FIG. 3 are normalized values from two experiments. It is important to note that at least 50% of the mice having B cells depleted, did not develop detectable metastases.

In summary, the results illustrated in Table 2, and FIG. 3 further support the finding that a host B cell response (pro-tumor immune response) is required for statistically significant promotion of tumor invasion and metastasis. Such host B cells may include those present in lymphoid tissues involved in a pro-tumor immune response, as detected by a detector molecule for the presence of shed tumor antigen, wherein such B cells have been activated by shed tumor antigen. Additionally, the results illustrated in Table 2, and FIG. 3 further support compositions and a method for depleting B cells which are involved in the progression of solid, nonlymphoid tumors by surgically removing lymphoid tissues involved in a pro-tumor immune response in a tumor bearing individual, or in an individual having a pro-tumor immune response.

EXAMPLE 3

Figure 4A:
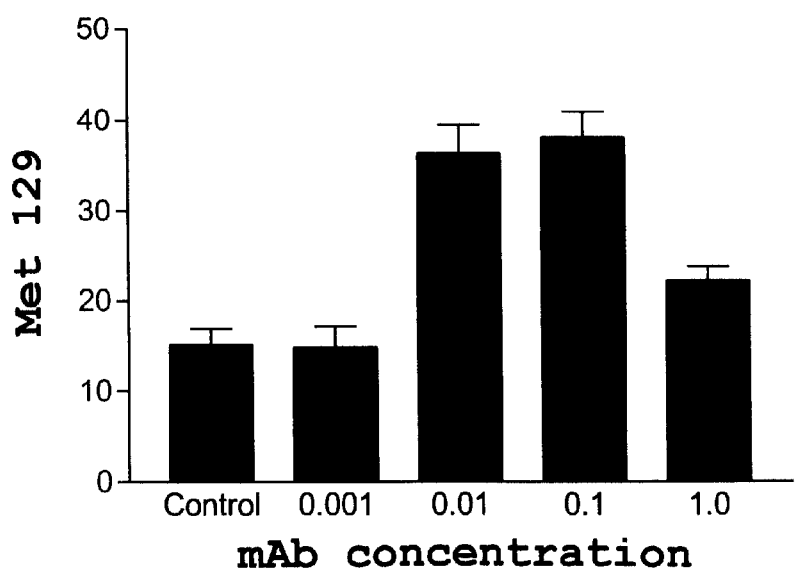
FIG. 4A is a bar graph of induction of Met 129 tumor cell growth in relation to concentration of added anti-shed tumor antigen antibody (in presence of shed tumor antigen).
Figure 4B:
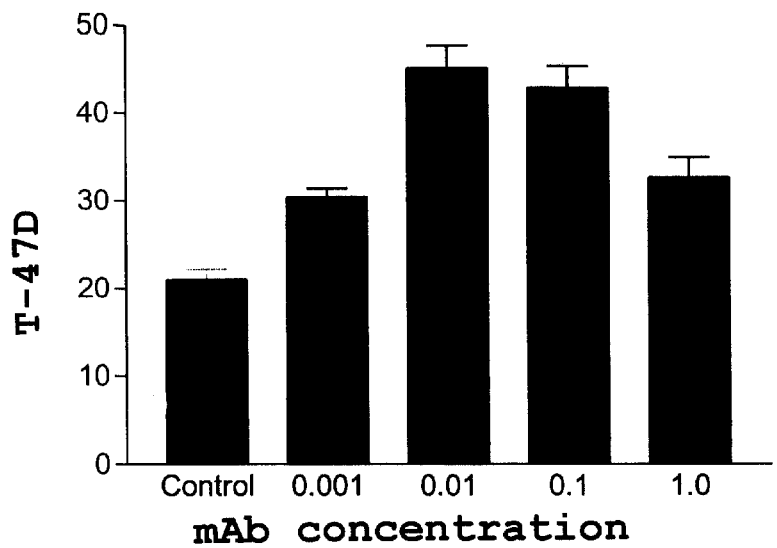
FIG. 4B is a bar graph of induction of T-47D tumor cell growth in relation to concentration of added anti-shed tumor antigen antibody (in presence of shed tumor antigen).

In this Example, illustrated is the ability of immune complexes consisting of shed tumor antigen and antshed tumor antigen antibody to promote tumor progression. In one aspect, immune complexes comprising anti-shed tumor antigen mAb and shed tumor antigen were shown to induce tumor cell growth. In this in vitro tumor cell proliferation assay, separately used were mucin-secreting tumor cell lines T-47D (human breast carcinoma) and Met129 (murine mammary carcinoma). The tumor cells were aliquoted into wells of a 96 well plate at 1000 cells per well for a total of 30 wells per cell line. Immediately following the seeding of the tumor cells, a concentration (either 0.001, 0.01, 0.1 and 1.0 μg) of dialyzed anti-sTn mAb or control medium was added to each well. After incubating the plates for approximately 72 hours at 37° C. in 5% $CO_2$, proliferation was assessed by counting adherent cells in each well. As shown in FIGS. 4A and 4B, anti-shed tumor antigen antibody (e.g., anti-sTn mAb), in the presence of shed tumor antigen (mucin) can promote growth of shed tumor antigen-secreting tumor lines. More particularly, the dependence on concentration of the anti-sTn mAb is characteristic of immune complex mediation of tumor growth; i.e., tumor growth is promoted most in conditions lacking antigen excess and antibody excess. Immune complex mediation of a pro-tumor immune response has also been confirmed by immunohisto-chemical analysis for shed tumor antigen and anti-shed tumor antigen antibody in tissue sections from standard animal models for tumor invasion and metastasis.

Figure 5:
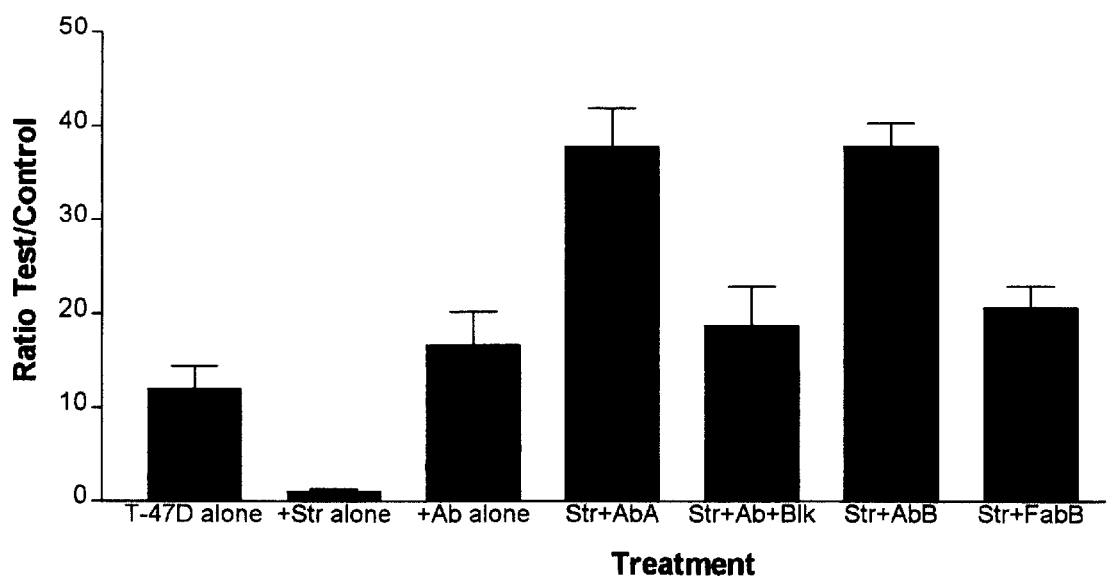
FIG. 5 is a bar graph illustrating invasion of shed tumor antigen-secreting tumor cells through matrix when incubated with various cellular components, antibodies, or antibody fragment.

In another aspect, immune complexes comprising anti-shed tumor antigen mAb and shed tumor antigen were shown to induce tumor cell invasion in the presence of murine stromal cells (granulocytes, macrophages, fibroblasts, and endothelial cells). In this in vitro tumor cell invasion assay, used were mucin-secreting human tumor cell line T-47D, a Boyden chamber, and a commercially available basement membrane matrix preparation ("matrix"). In this assay, tested was the ability of tumor cells ($2 \times 10^4$ cells) to migrate through the matrix in the following conditions: matrix alone; matrix containing stromal cells ($2 \times 10^5$ cells); matrix in the presence of anti-sTn mAb (0.06 $\mu$g); matrix containing stromal cells in the presence of anti-sTn mAb; and matrix containing stromal cells in the presence of Fab fragments of the anti-sTn mAb. The plates were incubated at 37° C. in 5% $CO_2$, and fresh media (with or without antibody, depending on the condition) was substituted every 24 hours. Invasion was measured by counting the number of tumor cells per well which migrated to the bottom of the chamber after 48 to 72 hours. FIG. 5 shows that the maximum invasion through the matrix was observed when the shed tumor antigen-secreting tumor cells were incubated in the presence of stromal cells and either of two anti-sTn mAb tested ("Str+AbA"; and "Str+AbB") as compared to tumor cells alone ("T-47D alone"), or stromal cells ("+Str alone"), or anti-sTn mAb ("+Ab alone"), or stromal cells in the presence of Fab fragments of the anti-sTn mAb (Str+FabB). These experiments are further evidence that shed tumor antigen secreted by tumor cells can interact with anti-shed tumor antigen antibody in forming complexes that can activate cells, such as granulocytes and macrophages, to secrete enzymes and factors (e.g., tissue degrading enzymes) that promote tumor progression. The involvement of immune complexes, as opposed to the action of antibody alone, was confirmed by using a tumor cell which did not produce sTn-containing shed tumor antigen; i.e., when such tumor cells were incubated in the presence of stromal cells and anti-sTn mAb, there was no increase in tumor invasion as compared to the control values.

EXAMPLE 4

This Example illustrates that shed tumor antigen is present in lymph nodes determined to be "false positive" during a procedure such as radioimmunoguided surgery. Forty colorectal carcinoma patients in a radioimmunoguided surgery protocol (using the methods outlined in U.S. Pat. No. 4,782,840) were assessed for the anatomical distribution of detector antibody comprising radiolabelled anti-mucin-1 monoclonal antibody. Positive detection (a signal of measurably greater intensity of strength than that of the background level of detector antibody) localized in the tumor, and also in abdominal lymph nodes, but not in a random distribution. All specimens, whether positive or negative by radioimmunoguided surgery, were examined histopathologically including histological staining (hematoxylin, eosin, and mucicarmine) using methods known in the art. The distribution of positive lymph nodes (which include false positives) are shown in Table 3, wherein +LN means lymph node positive for mucin-1, and as expressed relative to the number of patients assessed.

TABLE 3

| Stage | Upper Abdomen +LN | Middle Abdomen +LN | Lower Abdomen +LN | Regional +LN | Peripheral +LN |
|---|---|---|---|---|---|
| Stage I & II | 15/21 | 11/21 | 1/21 | 3/21 | 0/21 |
| Stage III | 16/19 | 14/19 | 6/19 | 9/19 | 0/19 |

By histologically staining of the lymph node specimens, it was determined that at least 80% of the positive lymph nodes did not contain evident tumor cells, but did contain shed tumor antigen in the germinal centers in a distribution consistent with presentation by follicular or germinal center dendritic cells. Additionally, the germinal centers of those positive lymph nodes always showed an intense B cell response. As to patients with either Stage I or Stage II disease, all of the positive lymph nodes lacked evident tumor cells. This is consistent with the definition of Stage I and Stage II disease in that evident tumor has yet to invade, or has very limited invasion into (i.e., only attachment to) surrounding tissues. However, shed tumor antigen would have more than ample opportunity to migrate into, and deposit in, surrounding tissues and distal tissues during Stage I or Stage II disease.

EXAMPLE 5

This Example illustrates an embodiment of the immune corrective procedure using a detector molecule. It will be appreciated by those skilled in the art that based on the following results, an effective amount of detector molecule (e.g., selected from the group consisting of a mAb, lectin, peptide or aptamer) may also be used effectively in the detection of shed tumor antigen-containing lymphoid tissues for surgical removal according to the method of the present invention. Immune corrective surgery may be used by itself, in conjunction with chemotherapy or radiotherapy, in conjunction with traditional surgical techniques, or in conjunction with radioimmunoguided surgery. In this illustration, immune corrective surgery was used in addition to radioimmunoguided surgery. Using $^{125}$I anti-mucin-1 mAb as the detector molecule for detecting localization of shed tumor antigen (mucin) in lymphoid tissues, a prospective clinical trial was performed with the following objective: to find, in a tumor bearing individual, lymphoid tissue containing shed tumor antigen; to remove from the tumor bearing individual such lymphoid tissue detected; and to postoperatively monitor the treated individual for survival from neoplastic disease.

In that regard, areas of lymphoid tissue not containing obvious tumor, as determined by palpation and inspection, but which showed increased radioactivity ($\geq 20$ counts per 2 seconds using a hand-held gamma detecting probe) when compared to adjacent areas of tissue with less radioactivity (<20 counts per 2 seconds), and which were in the general anatomic area of a tumor, were resected at the discretion of the surgeon. Post-operative follow-up included the evaluation of the clinical status and survival of individuals undergoing such treatment as compared to the clinical status and survival of individuals in which the detected lymphoid tissues practically could not be, or electively were not, resected.

Briefly, procedures for this clinical trial are as follows. Tumor bearing individuals having primary or recurrent colorectal carcinoma were selected. Anti-mucin-1 mAb was labeled using sodium iodide $^{125}$I using the 1,3,4,6- tetrachloro-3-alpha-diphenylglycouril method. Radiolabeled mAb was then purified by chromatography, and sterilized by filtration. $^{125}$I anti-mucin-1 mAb was then prepared in phosphate buffered saline in producing the detector molecule. Prior to administration of the detector molecule, multiple doses of a saturated solution of potassium iodide (e.g., 1 ml of a 500 mg/ml solution of KI) were given to the individual to block thyroid uptake of the detector molecule. Detector molecule (e.g., ranging from 0.2 mg to 10 mg) was administered intravenously. In a time period sufficient to establish a background level of radioactivity in the individual (e.g., about 21 days to about 28 days post-injection for a whole mAb), the individual underwent exploratory surgery in which a hand-held gamma detecting probe was used to detect radioactive lymphoid tissue (for immune corrective surgery). Each of the two groups of tumor-bearing individuals, having colorectal carcinomas homogenous in tumor staging, were surgically treated under a different protocol. A first treatment group comprised 34 patients who were subjected to radioimmunoguided surgery alone. This first treatment group included 9 stage I (AJCC staging) patients, 12 stage II patients, and 13 stage III patients. A second treatment group comprised 24 patients were treated with immune corrective surgery, and then also subjected to radioimmunoguided surgery. This second treatment group included 5 stage I patients, 6 stage II patients, and 13 stage III patients. For each group, radioimmunoguided surgery was performed to remove neoplastic tissue using a protocol as essentially described previously (see, e.g., U.S. Pat. No. 4,782,840).

Figure 6:
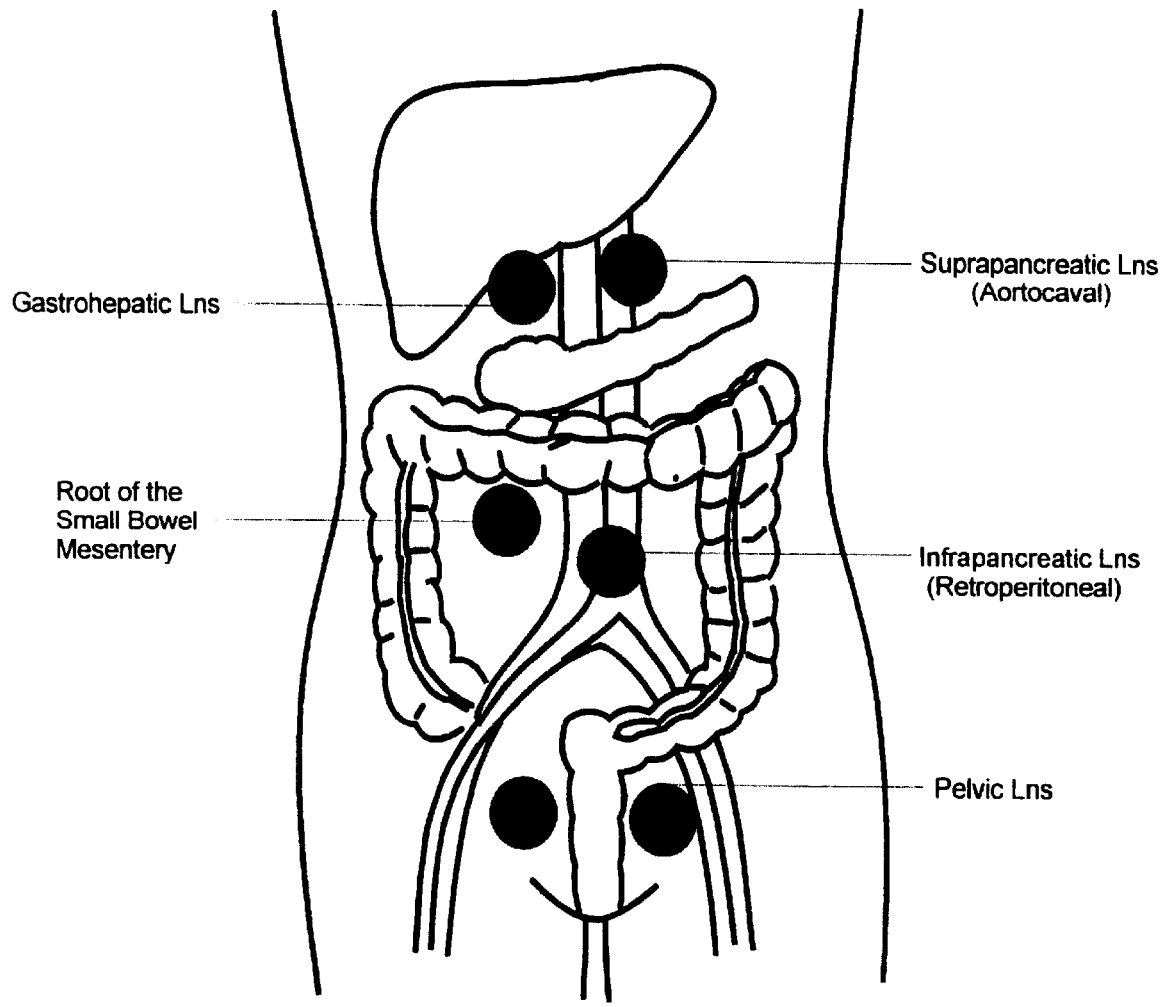
FIG. 6 is a graphic representation comprising a map of the approximate location of lymphoid tissues, including abdominal lymphoid tissues ("Lns"), in an individual.

In the immune corrective surgery, lymphoid tissues containing shed tumor antigen (as detected by the detector molecule) were removed from one or more of the areas selected from the group consisting of the gastrohepatic ligament, celiac axis, iliac vessels, retroperitoneum, or a combination thereof; areas or sites from which a surgeon would not traditionally remove tissue without obvious tumor. FIG. 6 provides a "lymphoid tissue" map which may be used to assist in identifying some of the lymphoid tissues contained with the abdominal region which may be frequently involved in a pro-tumor immune response as found using an effective amount of detector molecule to detect shed tumor antigen. After resection of the lymphoid tissues detected as containing shed tumor antigen, the areas around the excised lymphoid tissues were rescanned for residual radioactivity. The five year survival rate (free of clinically evident neoplastic disease) was calculated for each treatment group, and expressed as a percentage (Table 4, "5 yr."). Table 4 shows a comparison of the 5 year survival rate between colorectal tumor bearing individuals undergoing tumor removal by radioimmunoguided surgery only ("Group 1"); colorectal tumor bearing individuals undergoing immune corrective surgery to remove lymphoid tissues involved in a pro-tumor immune response, in addition to undergoing tumor removal by radioimmunoguided surgery ("Group 2"); and as compared to outcomes of traditional (standard) surgery for colorectal tumor bearing individuals as reported by the National Cancer Database ("T.Surg."). As shown in Table 4, tumor bearing individuals who received immune corrective surgery to remove lymphoid tissues containing shed tumor antigen, in addition to tumor removal by radioimmunoguided surgery, showed a statistically significant increase in 5 year survival as compared to tumor bearing individuals receiving either radioimmunoguided surgery alone, or traditional surgery alone. Of particular note is the significant improvement in 5 year survival for patients who had stage III (regionally disseminated) disease at the time of immune corrective surgery. In summary, the results in Table 4 clearly show that by not removing lymphoid tissue containing shed tumor antigen, patients' 5 year survival rates are statistically reduced (as compared to that of patients from which lymphoid tissue containing shed tumor antigen had been removed using immune corrective surgery).

TABLE 4

| Patients | # of patients | Stage | 5 yr. |
| --- | --- | --- | --- |
| Group 1 | 9 | I | 67% |
| Group 2 | 5 | I | 100% |
| T.Surg. | — | I | 68% |
| Group 1 | 12 | II | 42% |
| Group 2 | 6 | II | 100% |
| T.Surg. | — | II | 64% |
| Group 1 | 13 | III | 31% |
| Group 2 | 13 | III | 77% |
| T.Surg. | — | III | 44% |

Using the procedures in this illustration, an effective amount of detector molecule having binding specificity and affinity for a shed tumor antigen may be used to target and detect shed tumor antigen in lymphoid tissues involved in a pro-tumor immune response. Detection of lymphoid tissue containing shed tumor antigen by using the detector molecule is a prognostic indicator that an individual has an immune response (pro-tumor immune response) which can promote tumor progression (e.g., one or more of growth, invasion, and metastasis). As appreciated by those skilled in the art, the amount of detector molecule injected, and the time period sufficient to establish a background level of radioactivity (or signal) in the individual may vary depending on factors that may include the binding affinity and specificity of the detector molecule for shed tumor antigen, the efficiency of labeling the detector molecule with the detectable label, molecular size of the detector molecule, and clearance properties of the detector molecule. One skilled in the art would be able to determine an effective amount of detectable molecule to be administered. For purposes of illustration, but not limitation, an effective amount of detector molecule may be determined by a medical practitioner to be in a range of from about 1 µg/kg body weight to 1 mg/kg body weight or more.

EXAMPLE 6

This Example illustrates an embodiment of using a detector molecule according to the present invention, wherein the detector molecule is preferably a peptide having an amino acid sequence of SEQ ID NO:1, or a peptide comprising a portion thereof, which is labeled with a detectable label. It will be appreciated by those skilled in the art that based on the results in Example 5 herein, that an effective amount of detector molecule comprising a peptide may also be used effectively in the detection for removal of shed tumor antigen-containing lymphoid tissues. It was not known at the time of the invention that a detector molecule comprising a mAb may actually promote tumor progression, if it binds with shed tumor antigen to form immune complexes (see, e.g., FIGS. 4A, 4B, and 5). Thus, an unexpected result and benefit of a detector molecule comprising a labeled peptide according to the present invention, as compared to a detector molecule comprising a labeled antibody, is that the peptide lacks an Fc domain, thereby avoiding cross-linking of Fc receptors on either tumor cells and/or stromal cells or other Fc receptor bearing cells.

In one illustration, administered (e.g., bolus intravenous or parenteral injection) to an individual is an effective amount of detector molecule comprising the peptide identified by amino acid sequence, SEQ ID NO:1, or a peptide comprising a portion thereof (may include, but is not limited to, SEQ ID NOs: 2–6). The term "parenteral" includes administration intravenously (a preferred embodiment), but also may include intramuscularly, subcutaneously, rectally, vaginally, intra-lymphatic, or intraperitoneally. The peptide is labeled with $^{125}$I using a method known in the art (e.g., iodination reaction), purified (e.g., by chromatography), and then prepared in dosage form. In this illustration, a saturated potassium iodide solution is administered prior to administration of the detector molecule, and until surgery is completed, in an amount sufficient to substantially block thyroid uptake of the detector molecule. An effective amount of the detector molecule is administered intravenously to the individual. In a preferred embodiment, an effective amount of the detector molecule may be an amount in the range of from about 1 $\mu$g/kg body weight to about 25 $\mu$g/kg body weight. After a time period (from the time of administration of the detector molecule) sufficient to establish a background level of radioactivity in the individual (e.g., a time period selected from the group consisting of a time period in the range of about 6 hours to about 96 hours, less than 48 hours, less than 72 hours, and less than 96 hours, post-injection), the individual undergoes exploratory surgery in which a hand-held gamma detecting probe was used to detect radioactive lymphoid tissue (lymphoid tissue containing detector molecule bound to shed tumor antigen). In the immune corrective surgical method, lymphoid tissues containing shed tumor antigen (as detected by the detector molecule) are removed; e.g., tissues which a surgeon would not traditionally remove without evident tumor. Optionally, after resection of the lymphoid tissues detected as containing shed tumor antigen, the areas around the excised lymphoid tissues may be rescanned for residual radioactivity and for removal of lymphoid tissue (containing shed tumor antigen) detected as the source of the residual radio-activity.

EXAMPLE 7

In this embodiment, some additional considerations are provided for instruments or probes useful for detecting the detector molecule according to the present invention, in performing immune corrective surgery. Probes and instruments which may be useful with the compositions of the present invention include, but are not limited to, a hand-held probe, a laparoscopic probe, a colonoscopic probe, a gamma emission imaging instrument (e.g., gamma camera), a probe detecting a magnetic field, and a magnetic emission imaging instrument. Desirable features of the instrument or probe include, but are not limited to, dimensions, maneuverability, and composition suitable for the intended application (e.g., hand-held versus laparoscopic); a detecting means capable of detecting the signal emitted by the detector molecule, where detecting means may be controlled to detect a threshold level of signal (e.g., signal measurably greater than the background level), and may be modified to collimate the field of detection for precisely locating the source of the emitted signal; a converting means to convert the detected signal (e.g., measurably greater than background signal) to a transmission perceptible to the user (e.g., visual and/or audio); the ability to be sterilized if the probe is used within a body cavity; and a power source. As appreciated by those skilled in the art, additional design features may be incorporated depending on the intended application.

In regards to in vivo detection of radioactive emissions from an effective amount of detector molecule comprising a radiolabeled detector molecule according to the present invention, there are commercially available gamma probes which may be utilized. Hand-held gamma probes are known those skilled in the art (see, e.g., U.S. Pat. Nos. 4,782,840, 5,070,878, and 5,383,456) to include, but are not limited to, cadmium telluride probes, cadmium telluride alloy probes, sodium iodide probes, and the like. Laparoscopic probes and camera, also known to those skilled in the art (see, e.g., U.S. Pat. No. 5,383,456), may be used for in vivo detection of a radiolabeled detector molecule according to the present invention. Gamma cameras are known in the art to include a scintillation crystal or detector responsive to radiation stimuli in human glands or organs (see, e.g., U.S. Pat. Nos. 5,689,116 and 5,677,535). A gamma-detecting endoscopic probe has been described previously (see, e.g., U.S. Pat. No. 4,932,412) which can be inserted through an orifice such as the vagina or rectum for use in a body cavity to detect lymphoid tissues containing radiolabeled detector molecule bound to shed tumor antigen. These gamma cameras and endoscopic probes may be used for in vivo detection of a radiolabeled detector molecule according to the present invention.

As appreciated by those skilled in the art, to use an instrument or probe, the detector portion of the instrument or probe is positioned sufficiently adjacent to lymphoid tissue (scanning) so as to detect any detectable signal (e.g., radioactivity) emitted; wherein if shed tumor antigen is detectably present in the lymphoid tissue being scanned, a signal of measurably greater intensity or strength than that of the background level is detected, and subsequently the lymphoid tissue detected as containing shed tumor antigen may be surgically removed. As will be appreciated by those skilled in the art, in the process of localizing and identifying lymphoid tissue containing shed tumor antigen, the distance between the instrument or probe and the lymphoid tissue being scanned will depend on several factors including, but not limited to, the intensity and pattern of the signal emitted by the detector molecule, the sensitivity of the instrument or probe in detecting the signal emitted by the detector molecule, and the level and distribution of background signal. In general, when using a hand-held cadmium telluride gamma probe to detect the radioactive signal emitted by a detector molecule (e.g., comprising $^{125}$I labeled peptide having binding specificity for mucin-1), the distance between the probe detector window and the lymphoid tissue being scanned is the operable range of about 0 cm to about 1 cm. The probe detector window is the surface area of the detecting means (e.g. cadmium telluride crystal), which is used to detect the signal emission of the detector molecule.

For example, using a laparoscopic probe to detect shed tumor antigen containing-lymphoid tissues in the peritoneal cavity, the individual is administered (via blood vessels or lymphatic system using methods known to those skilled in the art) an effective amount of detector molecule according to the present invention, and then surgery occurs after an appropriate time period to have the detector molecule preferentially localize in the lymphoid tissues containing shed tumor antigen, and to establish background levels. Inserted through a cannula at a portal established in a quadrant of the abdominal wall is a laparoscopic probe. The laparoscopic probe is then maneuvered along, and in adjacency with, the colon in scanning the peritoneal cavity for lymphoid tissues containing shed tumor antigen, as indicated by the detection of signal (measurably greater than background signal) emitted by the detector molecule. The lymphoid tissues detected as containing shed tumor antigen may then be surgically removed by laparoscopic surgery. In the case where such lymphoid tissue is difficult to remove, an open laparotomy may be performed, and the areas rescanned to detect and remove lymphoid tissues containing shed tumor antigen.

Another embodiment is the detection of magnetic signals from a detector molecule comprising an affinity molecule, wherein affinity molecule has binding specificity for shed tumor antigen, and wherein the affinity molecule is bound to a magnetic particle. Magnetic particles that may be useful in producing the detector molecule according to the present invention may include ferromagnetic, ferri-magnetic, diamagnetic, and paramagnetic particles. Such particles may take the form of beads, crystals, micro-spheres, and the like. As appreciated by those skilled in the art, the size and composition of the magnetic particles may vary. It is generally known that magnetic particles in the range of 0.3 micron to 1 micron or greater, are rapidly cleared from the blood by the reticuloendothelial system primarily in the liver and spleen, thereby minimizing delivery to other tissues (e.g., lymphoid tissues). Accordingly, magnetic particles for use in vivo with the method according to the present invention include those less than 1 micron in diameter, and preferably 10 nanometers to 30 nanometers in diameter. Other properties of the magnetic particles desirable for in vivo use with the method of the present invention include that they be pharmacologically acceptable; either metabolizable or are metabolically inert; magnetically mapable; and able to concentrate in shed tumor antigen containing lymphoid tissues. To be pharmacologically acceptable, the magnetic particles need to be of an electrostatic nature so as to prevent intravascular clumping; and be biocompatible. Methods of making magnetic particles biocompatible are known to those skilled in the art. For example, magnetic particles may be coated with synthetic polymers (e.g., poly-L-lysine, poly-L-glutamic acid), protein or glycoprotein polymers (e.g., albumin, hemoglobin, gelatin), and polysaccharides (endogenous carbohydrates including starch, glycogen, and dextran) (collectively referred to as "polymers"; see, e.g., U.S. Pat. Nos. 4,247,406 and 5,670,135 for particle types, and coatings). In a related embodiment, the magnetic particles may be coated with both polymers and peptide. In a preferred embodiment, the magnetic particles are coated (noncovalently or covalently using methods known in the art) with a peptide having binding affinity and specificity for shed tumor antigen (e.g., SEQ ID NO:1, or a peptide comprising a portion thereof) in forming detector molecule in a manner that maximizes the presentation of the Tn antigen binding domain of the peptide to optimize interaction and binding with its Tn antigen ligand on shed tumor antigen. Coatings may be used to either optimize this type of binding of affinity molecule to the magnetic particles, and/or may be used to coat the magnetic particles on surfaces of the magnetic particles to which affinity molecule did not bind. Such coatings should be considered in the final size of the detector molecule which utilizes magnetic particles.

An effective amount of such detector molecule may be administered parenterally to the individual; e.g., intravascularly, and preferably into a blood vessel within a short distance of the anatomic site to be scanned. Alternatively, an effective amount of detector molecules are delivered to the lymph nodes and other lymphoid tissue by drainage of interstitially localized preparations through lymph vessels. The objectives of introducing the detector molecule include to maximize the amount of the detector molecule to shed tumor antigen containing-lymphoid tissues of the individual, thereby concentrating the magnetic signal to be detected from detector molecule binding to shed tumor antigen; and that detector molecule not specifically bound, be substantially cleared (blood circulation reduction) from the individual to achieve a background level of signal.

It will be appreciated by those skilled in the art, that an effective amount of the detector molecule administered, and the clearance from the blood circulation, may depend on such factors which include, but are not limited to, one or more of the character of the magnetic particle (including a coating if a coating is used) as to chemical and/or physical characteristics (e.g., ionic properties, size, shape, reactive groups), and interactions with other macromolecules and/or cells in the circulation. A sensitive magnetometer probe, capable of detecting the magnetic signal emitted by the effective amount of detector molecule bound to shed tumor antigen localized and concentrated in the lymphoid tissue scanned, may be used for one or more of (a) determining the distribution of detector molecules in shed tumor antigen-containing lymphoid tissue; (b) determining the time period for maximal detector molecule (comprising a coated magnetic particle) concentration in shed tumor antigen containing-lymphoid tissue; (c) detecting the achievement of a background level of signal; and (d) determining detector molecule (with magnetic particle) localization and concentration by differential comparisons of mappings taken over a time interval. The dosage of the detector molecule to be administered will vary depending on such factors including, but not limited to, those factors that relate to clearance from the blood circulation, the efficiency of binding the affinity molecule to magnetic particles, the availability of the shed tumor antigen binding domain(s) of the affinity molecule when bound to the magnetic particle, the strength of magnetic signal emitted from the magnetic particles, and the sensitivity of the magnetometer probe to detect the concentrated magnetic signal in shed tumor antigen-containing lymphoid tissue. One skilled in the art would be able to determine an effective amount of detectable molecule to be administered, and the time period necessary to achieve a background level of signal. For purposes of illustration, but not limitation, an effective amount of peptide, used to form an effective amount of the detector molecule, may be determined by a medical practitioner to be in a range of from about 1 $\mu$g/kg body weight to 1 mg/kg body weight or more. The amount of magnetic particles used to form an effective amount of detector molecule may also be determined by a medical practitioner. For example, intravenous injections of magnetic particles that have been used previously in the art include 1 to 10 mg of particles per kg of body weight of the patient, and up to 20 to 45 mg per kg of body weight (see, e.g., U.S. Pat. No. 4,735,796). Magnetometer probes which have been described as detecting magnetic particles in vivo are known in the art (see, e.g., U.S. Pat. Nos. 5,494,035; 5,444,372; and 5,384,109), and may be used in the method according to the present invention. According to this embodiment, detector molecule comprising peptide and magnetic particles may be used to detect shed tumor antigen containing lymphoid tissues, thereby enabling a surgeon to surgically remove all or that portion of that detected lymphoid tissue from the individual.

EXAMPLE 8

In addition to the peptide consisting of SEQ ID NO:1, various peptides comprising a portion thereof may be synthesized (or recombinantly produced) and tested for their ability to bind to the Tn antigen. For example, overlapping peptides (e.g., 15 to 40 amino acids in length) spanning the entire 116 amino acid sequence of SEQ ID NO:1 may be produced using one of the several methods of peptide synthesis known in the art. Peptide synthesis methods include standard solid phase peptide synthesis using tert-butyloxcarbonyl amino acids (Mitchell et al., 1978, *J. Org. Chem.* 43:2845–2852), 9-fluorenylmethyloxycarbonyl amino acids on a polyamide support (Dryland et al., 1986, *J. Chem. So. Perkin Trans. I.,* 125–137); by pepscan synthesis (Geysen et al., 1987, *J. Immunol. Methods* 03:259; 1984 *Proc. Natl. Acad. Sci. U.S.A.* 81:3998); by standard liquid phase peptide synthesis; or by recombinant expression vector systems. Regarding the latter, the nucleotide sequence encoding SEQ ID NO:1 was operatively cloned (using restriction enzyme sites NcoI and XhoI) into a plasmid vector in forming a recombinant vector such that when the recombinant vector is transformed into a suitable Escherichia coli host strain, and induction of the transformants resulted in peptide production, and wherein the peptide is produced with a histidine tag (polyhistidine tail) at one terminus of the peptide. Hence, the peptide can be purified during recombinant production by chromatography over a nickel-containing column, followed by washing, and elution, using methods known in the art.

The binding of the various peptides derived from SEQ ID NO:1 can be tested for binding to the Tn antigen of shed tumor mucin by using shed tumor mucin, or a similar Tn antigen-expressing molecule such as asialo (having sialic acid removed) bovine salivary mucin, as a ligand in a binding assay. For example, asialo bovine salivary mucin can be used to coat the wells of a micotiter plate. After blocking unbound portions of the microtiter well with a blocking agent (e.g., gelatin solution), a peptide is added to the well and incubated with the immobilized asialo bovine salivary mucin. The well is then washed to remove any unbound or nonspecifically bound peptide, and then anti-Tn antigen antibody conjugated to a detectable moiety is added to the well and allowed to incubate. The well is then again washed, and substrate for color development is added. If the peptide binds to the Tn antigen of the asialo bovine salivary mucin, there will be a noticeable difference in the binding of the anti-Tn antigen antibody conjugate in that well as compared to a control well in which no peptide was added, and as compared to a well in which a peptide was added but the peptide lacks detectable binding specificity to the Tn antigen. A similar assay can be performed, wherein the peptide to be tested for the ability to bind Tn antigen is directly conjugated.

In another embodiment, peptides derived from the amino acid sequence SEQ ID NO:1 may be produced and screened using a peptide display library, and using standard techniques known in the art. For example, a peptide display library may comprise either a recombinant ("combinatorial" or "random") phage display library (e.g., Smith, 1991, *Curr. Opin. Biotech.* 2:668–73; Stern et al., 1997, *FASEB J.* 11: 147–53), or a chemically synthesized ("combinatorial clustered amino acid") peptide library (e.g., Kramer et al., 1995, *Mol. Immunol.* 32:459–65). In screening a chemically synthesized peptide library, the peptides may be bound to a solid support, such as a continuous cellulose membrane. A peptide display library may be produced in various micro-organisms including, but not limited to, bacteria, yeast, and filamentous fungi, which are genetically engineered to serve as an expression vector system; and wherein a nucleotide sequence encoding the contiguous sequence of amino acids is inserted into the vector such that the encoded amino acid sequence is then expressed on the surface of an organism in forming a peptide display library (Smith, 1991, *Curr. Opin. Biotechnol.* 2:668–73). The multiple amino acids encoded typically comprise 15 random amino acids; however, the number can be varied easily. One preferred expression vector system is the phage display system wherein the nucleotide sequences are inserted just downstream from a coat protein signal peptide in the virion DNA, such that the recombinant phage are functional, yet they display on their surface the foreign amino acids encoded by the inserted sequence (Smith, 1985, *Science,* 228:1315–7; Parmley and Smith, 1988, *Gene,* 73:305–318; and Scott and Smith, 1990, *Science,* 249:386–390).

Double-stranded oligonucleotides can be synthesized using methods known in the art (Scott and Smith, 1990, supra; Devlin et al., 1990, *Science,* 249:404–6; and Cwirla et al., 1990, *Proc. Natl. Acad. Sci. USA* 87:6378–82), thereby producing a multitude of degenerate oligonucleotides which are useful for insertion into an expression vector to encode millions of different peptides. The degenerate oligonucleotides are synthesized to have at least one restriction site at each of their ends, wherein the restriction site is appropriately chosen for insertion into an expression vector. For example, the purified double-stranded oligonucleotides may be 60 bp long and have overhanging ends that may be ligated into a filamentous phage vector (e.g., fUSE5 vector of Scott and Smith et al., 1990, supra) which have been previously digested with an appropriate, compatible, restriction enzyme. Thereby, the inserts are cloned into the phage III gene, and the encoded amino acids are displayed as part of the pIII capsid protein of the virion (i.e., the inserts are operably linked to one or more control elements promoting expression of the pIII gene). The peptide display library may then be screened using a Tn antigen expressing molecule (e.g., shed tumor mucin isolated from culture supernatants of cultured tumor cells or tumor cell lines, or asialo bovine salivary mucin). The screening procedure ("biopanning") can be performed in a number of ways known in the art. When recombinant phage are used, the DNA is isolated from an individual recombinant phage which was screened and selected for its displayed peptide with binding specificity and affinity for Tn antigen. The DNA is then sequenced to determine the nucleotide sequence of the insert encoding the displayed peptide. The amino acid sequence of the peptide can then be deduced from the nucleotide sequence. Alternatively, if the peptide was selected from a chemically synthesized library, the amino acid sequence of the peptide may obtained by amino acid sequencing. The sequencing procedures used are standard methods using standard reagents as known to those skilled in the art. Modifications of the peptides, including additions and/or substitutions, may be performed using methods known in the art. Such modifications may be made to improve binding specificity and/or affinity for Tn antigen, particularly for Tn antigen on shed tumor antigen (e.g., shed tumor-associated mucin), and to allow for coupling to the peptide a detectable label in forming a detector molecule.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. An isolated and purified peptide comprising an amino acid sequence of about 10 contiguous amino acids of SEQ ID NO: 1, wherein said peptide is no more than 116 contiguous amino acids of SEQ ID NO: 1, and wherein the peptide binds to Tn antigen, but does not detectably bind to sTn antigen.

2. A detector molecule for use in detecting Tn antigen of shed tumor antigen expressing Tn antigen, the detector molecule comprising:

the peptide according to claim 1, wherein the peptide is bound to a detectable label, and the detectable label is selected from the group consisting of a radioisotope, and a magnetic molecule.

3. A detector molecule for use in localizing and binding to shed tumor antigen expressing Tn antigen, the detector molecule comprising:

the peptide according to claim 1, wherein the peptide is bound to a detectable label, and the detectable label is selected from the group consisting of a radioisotope, and a magnetic molecule.

4. The detector molecule of claim 2, wherein the shed tumor antigen is mucin.

5. The detector molecule of claim 3, wherein the shed tumor antigen is mucin.

* * * * *